(12) United States Patent
Arenas

(10) Patent No.: US 12,419,909 B2
(45) Date of Patent: Sep. 23, 2025

(54) HYPOCHLOROUS ACID INTRAVENOUS SOLUTION, PREPARATION, AND METHOD OF USE THEREOF

(71) Applicant: BIIOSMART TECHNOLOGIES LLC, Miami, FL (US)

(72) Inventor: Danyel Armando Arenas, Santander (CO)

(73) Assignee: BIIOSMART TECHNOLOGIES LLC, Miami, FL (US)

(*) Notice: Subject to any disclaimer, the term of this patent is extended or adjusted under 35 U.S.C. 154(b) by 767 days.

(21) Appl. No.: 17/431,234

(22) PCT Filed: Feb. 20, 2020

(86) PCT No.: PCT/US2020/018966
§ 371 (c)(1),
(2) Date: Aug. 16, 2021

(87) PCT Pub. No.: WO2020/172363
PCT Pub. Date: Aug. 27, 2020

(65) Prior Publication Data
US 2022/0133779 A1  May 5, 2022

Related U.S. Application Data

(60) Provisional application No. 62/807,787, filed on Feb. 20, 2019.

(51) Int. Cl.
*A61K 33/20* (2006.01)
(52) U.S. Cl.
CPC ..................... *A61K 33/20* (2013.01)
(58) Field of Classification Search
CPC .................................................. A61K 33/20
See application file for complete search history.

(56) References Cited

U.S. PATENT DOCUMENTS

| | | | |
|---|---|---|---|
| 5,731,008 | A | 3/1998 | Morrow |
| 7,090,753 | B2 | 8/2006 | Sumita |
| 8,367,120 | B1 | 2/2013 | Norton et al. |
| 8,663,705 | B2 | 3/2014 | Norton et al. |
| 8,728,537 | B2 | 5/2014 | Wannowius et al. |
| 8,877,257 | B2 | 11/2014 | Goldan et al. |
| 8,945,630 | B2 | 2/2015 | Calderon |
| 9,168,318 | B2 | 10/2015 | Alimi |
| 9,414,584 | B2 | 8/2016 | Panicheva et al. |
| 9,486,479 | B2 | 11/2016 | Northey |
| 9,642,876 | B2 | 5/2017 | Alimi |
| 9,867,849 | B2 | 1/2018 | Lange et al. |
| 9,918,477 | B2 | 3/2018 | Northey |
| 10,016,455 | B2 | 7/2018 | Alimi |
| 10,094,030 | B2 | 10/2018 | Rubinsky et al. |
| 2003/0185704 | A1 | 10/2003 | Bernard et al. |
| 2006/0039996 | A1 | 2/2006 | Palmer |
| 2007/0196357 | A1 | 8/2007 | Alimi et al. |
| 2009/0258083 | A1 | 10/2009 | Calderon |
| 2010/0166809 | A1 | 7/2010 | Northey et al. |
| 2012/0207853 | A1 | 8/2012 | Alimi et al. |
| 2012/0269904 | A1 | 10/2012 | Northey |
| 2013/0115307 | A1 | 5/2013 | Norton et al. |
| 2015/0119245 | A1 | 4/2015 | Robertson, Jr. et al. |
| 2017/0296578 | A1 | 10/2017 | Sampson et al. |
| 2018/0110803 | A1 | 4/2018 | Paz Garcia et al. |
| 2018/0177824 | A1 | 6/2018 | Almas |
| 2019/0216090 | A1 | 7/2019 | Alimi et al. |

FOREIGN PATENT DOCUMENTS

| | | |
|---|---|---|
| CN | 101932330 A | 12/2010 |
| KR | 20050039835 A | 4/2005 |
| WO | 2014015444 A1 | 1/2014 |
| WO | 2019006217 A1 | 1/2019 |

OTHER PUBLICATIONS

CDC Risk Factors Fungal Disease 2024.*
Extended European Search Report Search Report for Appl. No. 20759982.0-1112/3927351 PCT/US2020018966; Date of Mailing Dec. 6, 2022, 9 pages.
"Basic Chemisty of Chlorination", Hydro Instruments, Jul. 2010, 8 pages.
Captain John Fraser et al., "Further Observations on the Treatment of Gas Gangrene by the Inravenous Injection of Hypochlorous Acid (Eusol)", The British Medical Journal, Aug. 5, 1916, 3 pages.
Captain John Fraser et al., "Treatement of Acute Toxaemia Secondary to Gas Gangrene by the Intravenous Injection of a Solution of Hypochlorous Acid", The British Medical Journal, Jan. 15, 1916, 4 pages.
David Armstrong et al., "Expert recommendations for the Use of Hypochlorous Solution: Science and Clinical Application", Wounds:a compendium of clinical research and practice, May 2015, 20 pages.
Dmitri Debabov et al., "Avenova with Neutrox (pure 0.01% HOCLI) compared with OTC product (0.02% HOCl)", NovaBay Pharmaceuticals, Inc., May 2015, 5 pages.
Eryilmaz, Mujde et al.; "Hypochlorous Acid—Analytical Methods and Antimicrobial Activity"; Tropical Journal of Pharmaceutical Research, V. 12:1, Feb. 2013, p. 123-126.
H.D. Dakin, "The Behaviour of Hypochlorites on Intravenous Injection and their Action on Blood Serum", The British Medical Journal, Jun. 17, 1916, 3 pages.
International Search Report issued in Application No. PCT/US2020/018966 on May 15, 2020, 5 pages.
P.C. Vincent et al., "Evaluation of an Antitumor Cell Wound Irrigant-Milton, A Stable Hypochlorite", Cancer, vol. 17, Aug. 1964, 9 pages.
Ronald W. Pero et al., "Hypochlorous acid/N-chloramines are naturally produced DNA repair inhibitors", Carinogenesis, vol. 17, No. 1, 1996, 6 pages.

(Continued)

*Primary Examiner* — Shirley V Gembeh
(74) *Attorney, Agent, or Firm* — CANTOR COLBURN LLP

(57) ABSTRACT

Disclosed are intravenous solution compositions comprising hypochlorous acid (HOCl) suitable for systemic treatment or prevention of a variety of infections.

10 Claims, No Drawings

(56) References Cited

OTHER PUBLICATIONS

Shawnna Veasey et al., "Evaluation of Electrolytically-Generated Hypochlorous Acid ('Electrolyzed Water') for Sanitation of Meat and Meat-Contact Surfaces," Foods, vol. 5, No. 42, Jun. 13, 2016, 15 pages.
Written Opinion issued in Application No. PCT/US2020/018966 on May 15, 2020, 7 pages.

\* cited by examiner

HYPOCHLOROUS ACID INTRAVENOUS SOLUTION, PREPARATION, AND METHOD OF USE THEREOF

CROSS REFERENCE TO RELATED APPLICATIONS

This application is a National Stage application of PCT/US2020/018966, filed Feb. 20, 2020, which claims the benefit of U.S. Provisional Application No. 62/807,787, filed Feb. 20, 2019, both of which are incorporated by reference in their entirety herein for all purposes.

BACKGROUND

Antimicrobial drugs, including antibiotics, have been developed over the years to successfully treat patients with infections. Certain bacteria and other infectious organisms develop resistance to treatment to these antimicrobial drugs, rendering them ineffective. The growth of infectious diseases, particularly treatment resistant bacteria, fungus and viruses, have raised a serious concern of the future of patient care.

Thus, there remains a need for new treatments for infectious diseases that are effective, safe, and non-toxic while avoiding the development of microbial resistance.

SUMMARY

Disclosed, in various embodiments, are hypochlorous acid (HOCl) intravenous solutions, kits comprising the solutions and methods of using the solutions for the treatment or prevention of infections.

In an embodiment, an intravenous solution composition, comprises about 0.010% to about 0.040% hypochlorous acid (HOCl); about 0.05 to about 0.35% in NaCl; about 0.005% to about 0.020% in OCl; and water, wherein all the % are by percentage over the total volume of the intravenous solution, and wherein the composition has a pH of about 5.2 to about 6.2.

In another embodiment, a kit comprises the intravenous solution composition packaged in a container and optionally further comprising information for providing the intravenous solution composition to a subject in need thereof.

In yet another embodiment, a method of treating an infection comprises providing an effective amount of the intravenous solution composition to a subject in need thereof. The infection can be bacterial, fungal, viral, bacterial spore, parasitic or a combination thereof.

These and other features and characteristics are more particularly described below.

DETAILED DESCRIPTION

Disclosed herein is a novel microbicidal hypochlorous acid (HOCl) solution for intravenous use designed to treat or prevent a wide range of infectious diseases including multidrug resistant bacteria, fungus, and viruses in a subject while maintaining a high degree of safety and biocompatibility. The hypochlorous acid intravenous solution can treat a number of infectious diseases naturally and with high efficacy, without causing bacterial resistance, toxicity, or adverse or secondary effects in the subject under treatment. The use of a non-toxic intravenous solution can be inoculated intravenously and the hypochlorous acid is a non-organic small molecule antibiotic/antifungal antimicrobial.

Hypochlorous acid is the major inorganic bactericidal compound in innate immunity. Hypochlorous acid is an endogenous molecule which is produced by neutrophils and macrophages as part of the innate immune cascade response to an invading pathogen into a process called "Respiratory Burst". The compound acts as a powerful oxidant and potent microbicidal agent within cellular immune response, with a high barrier to resistance. Thus, the intravenous solution employs a compound already found in the immune system albeit in a higher concentration.

HOCl induces irreversible chlorination and oxidation of microbial components including cell wall proteins such as peptidoglycan and respiratory electron transporters (ATP), and may also neutralize harmful endo and exo toxins as lipopolysaccharides (LPS) and gingipains.

HOCl, through oxidation processes, stimulate the production of cellular growth factors, such as insulin-like growth factor, epidermal growth factor, keratinocyte growth factor (also called FGF-7), FGF-1, FGF-2, TGF-β, PDGF, vascular endothelium growth factor, connective tissue growth factor as well many growth factors associated to oral health. Furthermore, hypochlorous acid can activate the transforming growth factor TGF-β, a reparative mediator that promotes tissue repair and fibrosis.

HOCl can also cause oxidation and chlorination of the amino acid taurine to yield taurine N-chloramine (TauCl). Oxidation reactions on taurine are more rapid than chlorination reactions and involve thioether and/or thiol groups of proteins. The formation of TauCl seem to play an important role in the regulation of the proteolytic enzymes and metalloproteinases, reducing the impact of these enzymes on the tissue destruction.

Stabilized hypochlorous acid (HOCl) solution is employed as the active ingredient in the intravenous solution. The hypochlorous acid solution maintains its stability and composition in organic matter (e.g., blood) for extended periods of time. The stabilized hypochlorous acid solution can be provided in a glass vial (ampoule) having a long shelf life (3 months or more), at temperatures below 30° C.

The microbicidal hypochlorous acid (HOCl) intravenous solution composition comprises about 0.010% to about 0.040% hypochlorous acid (HOCl), specifically about 0.020% to about 0.030% hypochlorous acid (HOCl), more specifically about 0.022% to about 0.028% hypochlorous acid (HOCl), and water, wherein each % is by percentage over the total volume of the intravenous solution, and the composition has a pH of about 5.2 to about 6.2. The intravenous solution composition further comprises about 0.05 to about 0.35% in NaCl, specifically about 0.15 to about 0.25% in NaCl, and more specifically about 0.18 to about 0.22% in NaCl, wherein each % is by percentage over the total volume of the intravenous solution. The intravenous solution composition further comprises about 0.005% to about 0.020% in OCl, specifically about 0.010% to about 0.020% in OCl, and more specifically about 0.012% to about 0.018% in OCl, wherein each % is by percentage over the total volume of the intravenous solution.

The microbicidal hypochlorous acid (HOCl) intravenous solution composition comprises, consists essentially of, or consists of, about 0.020% to about 0.030% hypochlorous acid (HOCl); about 0.15 to about 0.25% in NaCl; about 0.010% to about 0.020% in OCl; and water, wherein the composition has a pH of about 5.2 to about 6.2.

The hypochlorous acid (HOCl) intravenous solution composition comprises, consists essentially of, or consists of, about 0.020% to about 0.030% hypochlorous acid (HOCl), specifically about 0.020%, about 0.021%, about 0.022%, about 0.023%, about 0.024%, about 0.025%, about 0.026%, about 0.027%, about 0.028%, about 0.029%, about 0.030% or any range in between using any of the recited amounts as an upper or lower endpoint, e.g. about 0.022 to about 0.028%.

The hypochlorous acid (HOCl) intravenous solution composition comprises, consists essentially of, or consists of, about 0.15 to about 0.25% in NaCl, specifically about 0.15%, about 0.16%, about 0.17%, about 0.18%, about 0.19%, about 0.20%, about 0.21%, about 0.22%, about 0.23%, about 0.24%, about 0.25% or any range in between using any of the recited amounts as an upper or lower endpoint, e.g. about 0.18 to about 0.22%.

The hypochlorous acid (HOCl) intravenous solution composition comprises, consists essentially of, or consists of, about 0.005% to about 0.020% in OCl, specifically about 0.005%, about 0.006%, about 0.007%, about 0.008%, about 0.009%, about 0.010%, about 0.011%, about 0.012%, about 0.013%, about 0.014%, about 0.015%, about 0.016%, about 0.017%, about 0.018%, about 0.019%, about 0.020%, or any range in between using any of the recited amounts as an upper or lower endpoint, e.g. about 0.009 to about 0.015% or about 0.012 to about 0.018%.

The microbicidal hypochlorous acid (HOCl) intravenous solution composition has a pH of about 5.2 to about 6.2. Specifically, the pH of the intravenous solution composition can be about 5.2, about 5.3, about 5.4, about 5.5, about 5.6, about 5.7, about 5.8, about 5.9, about 6.0, about 6.1, about 6.2, or any range in between using any of the recited pHs as an upper or lower endpoint, e.g. about 5.5 to about 6.0. A pH in the range of about 5.2 to about 6.2 was found to provide surprising benefits for the administration of the intravenous solution to subjects. During administration, an HOCl solution having a pH around 7.4 reacts with red blood cells and can cause the vein to stiffen and become hard. Repeated administration of this higher pH solution was problematic, resulting in irritation at the site of administration. By lowering the pH of the intravenous solution composition to about 5.2 to about 6.2, the adverse effects were drastically decreased. The result was surprising as a pH around 7.4 would match the pH of blood and thus expected to be administered without problems. However, after the subjects experienced adverse symptoms at the elevated pH, the pH of the solution was lowered to about 5.2 to about 6.2 with surprising improvement in the reduction of irritation even after repeated administration. The pH of the vehicle used to administer the HOCl solution can be matched to the pH of the intravenous solution composition. The adverse effects were further reduced by maintaining OCl levels in the intravenous solution to less than 0.01%.

The intravenous solution can be used to treat, prevent, or eliminate a wide range of pathogens and microorganisms including virus, bacteria, bacterial spores, parasites, fungal or a combination thereof in a subject in need thereof. The hypochlorous acid intravenous solution is effective against antibiotic-resistant, antifungal-resistant, and antiviral-resistant species.

It has been discovered that the intravenous solution disclosed herein produces a positive immunogenic response, especially in immunocompromised animals. HOCl is an oxidant that is produced by the body's innate and adaptive immune response to an invading pathogen. HOCl is an endogenous molecule that belongs to the reactive oxygen species group that is traditionally understood to create a pro-inflammatory response. However, these models have mostly been analyzed under natural secretion and production circumstances in the body and not one of foreign administration. Not wishing to be bound by theory, but based on the present studies, it is believed the additive intravenous solution through protein chlorination utilizes classical and non-classical secretory pathways and signal peptides to decrease immunosuppression, act as an immunogenic and/or immunomodulatory solution in subjects who are clinically diagnosed with a condition and/or are immunocompromised. It may be considered a more natural adjuvant to the immune system stimulating a response of neutrophils (CD11b+, Ly6G+), eosinophils (CD11b+, CD11c$^{low/-}$, Siglec F$^+$), basophils (CD4−, CD19−, CD49b+, CD200R3+, FcεRIα+), mast cells8 (FcεRIα+ ckit+); macrophages (CD11b+, F4/80+) as well as lymphocytes, CD4 and CD8 T cell and B cells (CD25 will be used as an activation marker for lymphocytes) and dendritic cells (CD11c+CD11b+IA/IE+) and fibroblasts.

Exemplary bacterial infections that may be treated or prevented include those caused by gram negative bacteria, gram positive bacteria, *Escherichia coli, Campylobacter rectus, Enterobacter cloacae, Enterococcus faecalis, Enterococcus faecium, Klebsiella oxytoca, Klebsiella pneumoniae, Staphylococcus aureus*, methicillin-resistant *Staphylococcus aureus, Pseudomonas aeruginosa, Salmonella enteritidis, Staphylococcus epidermidis, Streptococcus pyogenes, Treponema pallidum* (syphilis), vancomycin-resistant enterococci, or a combination thereof.

Exemplary viral infections that may be treated or prevented include those caused by Herpes simplex virus type-2 and type-1, human immunodeficiency virus (HIV), human papilloma virus (HPV), Hepatitis B and C virus, Bovine Diarrhea virus, molluscum contagiosum, respiratory viruses such as influenza viruses (e.g. H1N1), coronavirus, Zika virus, Ebola virus, and the like.

Exemplary fungal infections that may be treated or prevented include those caused by *Aspergillus niger, Candida albicans, Trichophyton mentagrophytes*, and the like.

Exemplary parasitic infections that may be treated or prevented include those caused by trichomoniasis, leishmaniasis, and the like.

In an embodiment, the hypochlorous acid intravenous composition is free of or substantially free of one or more of sodium hypochlorite (NaHClO$_3$), ozone (O$_3$), hydrogen peroxide (H$_2$O$_2$), sodium hydroxide (NaOH), or a combination thereof.

The hypochlorous acid intravenous composition can be used as is or combined with a pharmaceutically acceptable parenteral vehicle or excipients to form a diluted intravenous solution composition. Exemplary pharmaceutically acceptable parenteral vehicles include water for injection (WFI), specifically sterile, nonpyrogenic, distilled water such as Sterile Water for Injection, USP, sterile; nonpyrogenic, isotonic solution of sodium chloride and water for injection; and the like. In an embodiment the vehicle is saline for intravenous infusion. Exemplary pharmaceutically acceptable parenteral excipients include those suitable for injection purposes such as a buffer, sodium chloride, potassium chloride and the like.

In an embodiment, when the hypochlorous acid intravenous composition is diluted and administered with a pharmaceutically acceptable parenteral vehicle or excipient, the resulting solution has a pH of about 5.2 to about 6.2.

Hypochlorous acid can be prepared using techniques and procedures known in the art, including chemical and electrochemical techniques. Exemplary processes include Hydrolysis of chlorine gas $Cl_2 + H_2O \rightarrow HOCl + H^+ + Cl^-$; or Electrolysis of a salt solution $2Cl^- + 2e^- \rightarrow Cl_2 + H_2O \rightarrow HOCl + H^+ + CL^-$; or Acidification of hypochlorite $OCl^- + H^+ \rightarrow HOCl$.

The intravenous solution composition can have a shelf life of up to 1 month, 2, 3, 4, 5, 6, 7, 8, 9, 10, 11, 12 months or more when packaged in a sterile glass vial and stored under conditions of 20° C. In an embodiment, the intravenous solution composition can have a shelf life of about 1 month to about 12 months, specifically up to about 3 to about 6 months.

The hypochlorous acid composition can be formulated for administration intravenously.

The intravenous solution composition can be packaged in unit dosage amounts for direct use or designed for mixing and diluting with commercially available intravenous solution vehicles on site, immediately prior to use as needed. The unit dosage amounts can be a volume of about 1 milliliter (ml) or more of the undiluted intravenous solution composition, specifically about 2 ml to about 100 ml, more specifically about 5 ml to about 75 ml, yet more specifically about 10 ml to about 50 ml, and still yet more specifically about 15 ml to about 30 ml. In an embodiment, a unit dosage amount is about 10 ml of the undiluted intravenous solution composition. The unit dosage amounts can be packaged in containers that maintain the intravenous solution composition sterile, pyrogen-free, stable, and pure prior to use, for example sterile glass vials (ampoules), plastic vials, and the like.

In an embodiment, a kit comprises, consists essentially of, or consists of the intravenous solution composition as disclosed herein packaged in one or more containers and optionally further comprising information for providing the intravenous solution composition to a subject in need thereof. In an embodiment, a kit comprises a unit dosage amount of about 10 ml of the undiluted intravenous solution composition, about 90 ml of a vehicle, and optionally instructions for its use.

The hypochlorous acid intravenous solution can be used in a non-toxic method to fight diseases caused by bacteria, bacterial spores, viruses, parasites, or a combination thereof, including those described herein The intravenous solution can be used to treat systemic infections or localized infections.

The hypochlorous acid intravenous solution may also be administered to a subject to augment the subject's immune system, specifically those subjects having an infectious disease, subjects at risk of contracting an infectious disease, subjects receiving cancer treatment, chemotherapy, radiation therapy, surgery, and the like, or a combination thereof.

In an embodiment, the hypochlorous acid intravenous solution may be provided to a subject for the treatment of a cancer or provided to a subject that is undergoing cancer treatment with another anticancer agent, chemotherapy, radiation therapy, or a combination thereof.

"Cancer" as used herein can refer to adenocarcinomas, carcinomas, leukemias, lymphomas, sarcomas, solid and lymphoid cancers, and the like. Examples of different types of cancer include, acute lymphocytic leukemia (acute lymphoblastic leukemia), acute myeloid leukemia (acute myelogenous leukemia, acute myeloblastic leukemia, acute myelocytic leukemia, acute granulocytic leukemia, and acute nonlymphocytic leukemia), anal cancer, B-cell lymphoma, bile duct cancer, bladder cancer, blood cancer, breast cancer, Burkitt's lymphoma, central nervous system cancer, cervical cancer, choriocarcinoma, chronic lymphocytic leukemia, chronic myeloid leukemia (chronic myelogenous leukemia), colorectal cancer, esophageal cancer, fibrosarcoma, gall bladder cancer, gastrointestinal carcinoid tumors, glioma, head and neck cancer, Large Cell lymphoma, liposarcoma, liver cancer (i.e., hepatocarcinoma), lung cancer (e.g., non-small cell lung cancer or NSCLC), melanoma, monocytic leukemia, multiple myeloma, myelodisplastic syndromes (MDS), myelogenous leukemia, neuroblastoma, non-Hodgkin's lymphoma, ovarian cancer, osteogenic sarcoma, pancreatic cancer, pleural cancer, prostate cancer, renal cancer (i.e., renal cell carcinoma), skin cancer, Small Cell lymphoma, small intestine cancer, stomach (gastric) cancer, testicular cancer, thyroid cancer, uterine cancer, and the like.

Exemplary anticancer agents that can be provided to the subject while receiving hypochlorous acid intravenous therapy include, alkylating agents such as alkyl sulfonates (e.g., busulfan), ethylenimines (e.g., altretamine, thiotepa), nitrogen mustards (e.g., bendamustine, chlorambucil, cyclophosphamide, ifosfamide, mechlorethamine, melphalan), nitrosoureas (e.g., carmustine, lomustine, streptozocin), and triazines (e.g., dacarbazine, temozolomide); an antimetabolite such as azacitidine, capecitabine. cladribine, clofarabine, cytarabine, decitabine, fludarabine, fluorouracil, gemcitabine, mercaptopurine, nelarabine, pemetrexed, pentostatin, thioguanine and the like; anti-microtubule agents such as colchicine, vinca alkaloids and taxanes (e.g. docetaxel, paclitaxel, taxane, vinblastine, vincristine, vinorelbine), and the like; topoisomerase inhibitors such as aclarubicin, camptothecin, doxorubicin, etoposide, irinotecan, merbarone, mitoxantrone, novobiocin, teniposide, topotecan, and the like; and cytotoxic antibiotics such as aclarubicin, actinomycin, anthracyclines, bleomycins, daunorubicin, doxorubicin, epirubicin, idarubicin mitomycin C, mitoxantrone, pirarubicin, and the like.

In an embodiment, the hypochlorous acid intravenous solution may be provided to a subject for use as a prophylaxis to prevent bacterial or fungal contamination, bacterial or fungal infection, or sepsis during large-volume intravenous therapy (100 mg or more) or intravenous feeding in a subject. For example, cancer patients or burn patient receiving long term intravenous therapy with one or more other therapeutic agents can be pre-treated or concurrently treated with the hypochlorous acid intravenous solution.

As used herein, the subject or patient can be a mammal. A mammal includes humans, companion animals, and livestock. In a specific embodiment, the mammal is a human.

The term "providing", as used herein, means giving, administering, selling, distributing, transferring (for profit or not), manufacturing, compounding, or dispensing.

The term "treatment", as used herein, includes providing the intravenous solution composition to a subject to: (a) prevent an infection or a symptom of an infection from occurring in a subject who may be at risk for contracting an infection but has not yet been infected; (b) inhibiting the infection, i.e. arresting its development; and (c) eliminating the infection or ridding the subject of the infectious organism or virus. The infection may be from a virus, a bacteria, a bacterial spore, a parasite, a fungus, or a combination thereof.

The term "therapeutically effective amount" of an intravenous solution composition, as used herein, means an amount effective, when administered to a subject, to provide a therapeutic benefit such as an amelioration of symptoms, e.g., to treat a subject suffering from an infection or to prevent an infection.

In an embodiment, the intravenous solution composition can be provided to the subject for the methods described herein in an amount effective for carrying out the particular method. For example, the intravenous solution composition can be provided in amounts of about 1 to about 20 ml of the intravenous solution composition 0.5, 1, 2, 3, 4, or more times a day specifically about 1 ml, about 2 ml, about 3 ml, about 4 ml, about 5 ml, about 6 ml, about 7 ml, about 8 ml, about 9 ml, about 10 ml, about 11 ml, about 12 ml, about 13 ml, about 14 ml, about 15 ml, about 16 ml, about 17 ml, about 18 ml, about 19 ml, about 20 ml of the intravenous solution composition or any range in between using any of the recited amounts as an upper or lower endpoint, e.g. about 5 ml to about 15 ml. Within this embodiment, the intravenous solution composition is further diluted with a pharmaceutically acceptable parenteral vehicle to a diluted volume that is greater than the volume of the intravenous solution composition. Further within these embodiments, the intravenous solution composition, optionally diluted, can be provided to the subject for 1, 2, 3, 4, 5, 6, 7, 8, 9, 10, 11, 12 days or more, for 1, 2, or 3 weeks or more. In an embodiment, the intravenous solution composition is provided to a subject in need thereof in an amount of about 1 to about 20 ml, specifically about 10 ml of the intravenous solution composition once per day for a total of about 4 to about 6 doses; or once every 24 or 48 hours for a total of about 4 to about 6 doses. Within this embodiment, the intravenous solution composition is diluted in up to 100 ml of a pharmaceutically acceptable intravenous vehicle, specifically about 20 to about 85 ml of a pharmaceutically acceptable intravenous vehicle prior to administration to form a diluted intravenous solution composition.

In an embodiment, the intravenous solution composition, optionally diluted, can be provided to the subject in 1 dose every 24 to 48 hours for a total of about 4 to about 6 doses as a general dose, for combination therapy, to treat a bacterial infection, or for one time use. Each dose of the intravenous solution composition may be in an amount of about 1 to about 20 ml, specifically about 10 ml of the intravenous solution composition, optionally diluted with a pharmaceutically acceptable intravenous vehicle up to about 100 ml total volume.

In another embodiment, the intravenous solution composition, optionally diluted, can be provided to the subject in 2 doses weekly for 2, 4, 6, 8, 10, or 12 weeks, or until conditions improve, for a chronic condition, a viral infection, a combination therapy, or cancer. Within this embodiment, the subject may receive a loading dose during week 1, for example 1 dose for 4 days during week 1. Each dose of the intravenous solution composition may be in an amount of about 1 to about 20 ml, specifically about 10 ml of the intravenous solution composition, optionally diluted with a pharmaceutically acceptable intravenous vehicle up to about 100 ml total volume.

In another embodiment, the intravenous solution composition, optionally diluted, can be provided to the subject as 1 dose daily for 8 days for an urgent condition (e.g., bacterial/fungal sepsis). Each dose of the intravenous solution composition may be in an amount of about 1 to about 20 ml, specifically about 10 ml of the intravenous solution composition, optionally diluted with a pharmaceutically acceptable intravenous vehicle up to about 100 ml total volume.

The intravenous solution composition may be used in treatment alone or in combination with another therapeutic agent. Exemplary other therapeutic agents include antibacterials, antivirals, antiretrovirals (including highly active antiretroviral therapy (HAART) agents), anthelmintic agents, immunotherapy agents, a combination thereof, and the like. When used in combination therapy with another therapeutic agent, the intravenous solution composition is administered separately from the other therapeutic agent. In an embodiment, the intravenous solution composition is used in combination therapy for immunotherapy or for the treatment of HIV.

The following examples are merely illustrative of the effects of hypochlorus acid solutions against microorganisms and viruses, and the solutions' biocompatibility and safety, and are not intended to limit the scope hereof.

EXAMPLES

Example 1. Antimicrobial Spectrum of HOCl Solution

Table 1. below represents the efficacy of 0.046% aqueous hypochlorous acid solution in the presence of high organic load. ASTM E2315 Time Kill Assay for Antimicrobial Agents. Table 1. shows an efficacy of 99.999% for all microorganisms tested at a concentration of 0.046% in 30 seconds. Additional times were evaluated: 1 minute, 5 minutes, and 10 minutes, all with and without organic soil (Using 10% whole milk and 5% Fetal Bovine Serum). The trend in the efficiency is maintained under the same proportions.

TABLE 1

| Antiseptic Ability | Efficacy at 30 seconds | | | |
|---|---|---|---|---|
| | Control of Innoculum | | After treatment with 0.046% HOCl aqueous solution | |
| Microorganism | Population | Log | Log Reduction | % Reduction |
| A. baumanii | $7.1 \times 10^6$ | $6.85 \, \text{Log}_{10}$ | $>6.15 \, \text{Log}_{10}$ | 99.999% |
| E. faecium | $1.05 \times 10^6$ | $6.02 \, \text{Log}_{10}$ | $>5.32 \, \text{Log}_{10}$ | 99.999% |
| E. coli | $3.7 \times 10^6$ | $6.57 \, \text{Log}_{10}$ | $>5.87 \, \text{Log}_{10}$ | 99.999% |
| K. pneumoniae | $1.46 \times 10^6$ | $6.16 \, \text{Log}_{10}$ | $>5.46 \, \text{Log}_{10}$ | 99.999% |
| MRSA | $3.79 \times 10^6$ | $6.59 \, \text{Log}_{10}$ | $>5.89 \, \text{Log}_{10}$ | 99.999% |
| VRE | $1.62 \times 10^6$ | $6.21 \, \text{Log}_{10}$ | $>5.51 \, \text{Log}_{10}$ | 99.999% |
| S. aureus | $1.13 \times 10^6$ | $6.05 \, \text{Log}_{10}$ | $>5.35 \, \text{Log}_{10}$ | 99.999% |
| E. coli NDN-1 | $1.47 \times 10^6$ | $6.17 \, \text{Log}_{10}$ | $>5.47 \, \text{Log}_{10}$ | 99.999% |
| K. pneumoniae NDM-1 | $1.94 \times 10^6$ | $6.29 \, \text{Log}_{10}$ | $>5.59 \, \text{Log}_{10}$ | 99.999% |

TABLE 1-continued

| | | Efficacy at 30 seconds | | |
|---|---|---|---|---|
| Antiseptic Ability | Control of Innoculum | | After treatment with 0.046% HOCl aqueous solution | |
| Microorganism | Population | Log | Log Reduction | % Reduction |
| S. aureus Linezolid Resistant | $3.5 \times 10^6$ | $6.54 \text{ Log}_{10}$ | $>5.84 \text{ Log}_{10}$ | 99.999% |
| Candida albicans | $7.7 \times 10^6$ | $5.89 \text{ Log}_{10}$ | $>5.19 \text{ Log}_{10}$ | 99.999% |
| Enterobacter aerogenes | $4.0 \times 10^6$ | $6.60 \text{ Log}_{10}$ | $>5.90 \text{ Log}_{10}$ | 99.999% |
| Trichophyton mentagrophytes | $4.2 \times 10^6$ | $5.62 \text{ Log}_{10}$ | $>4.92 \text{ Log}_{10}$ | 99.999% |
| Haemophilus influenzae | $3.2 \times 10^5$ | $5.51 \text{ Log}_{10}$ | $>4.81 \text{ Log}_{10}$ | >99.99% |
| S. pyrogenes | $4.7 \times 10^5$ | $5.67 \text{ Log}_{10}$ | $>4.97 \text{ Log}_{10}$ | >99.99% |
| E. coli Carbapenem Resistant | $1.86 \times 10^6$ | $6.27 \text{ Log}_{10}$ | $>5.57 \text{ Log}_{10}$ | 99.999% |
| K. oxytoca | $1.99 \times 10^6$ | $6.30 \text{ Log}_{10}$ | $>5.50 \text{ Log}_{10}$ | 99.999% |
| K. pneumoniae-ESBL | $2.90 \times 10^6$ | $6.46 \text{ Log}_{10}$ | $>5.76 \text{ Log}_{10}$ | 99.999% |
| P. mirabilis | $2.26 \times 10^6$ | $6.35 \text{ Log}_{10}$ | $>5.65 \text{ Log}_{10}$ | 99.999% |
| S. Epidermidis | $1.98 \times 10^6$ | $6.30 \text{ Log}_{10}$ | $>5.60 \text{ Log}_{10}$ | 99.999% |

Example 2. Test of Viral Inactivation (Active Virucide)

Studies on the virucidal ability of a 0.046% HOCl aqueous solution was tested according to the "Standard Test Method for Efficacy of Antimicrobial Agents Against Viruses in Suspension" (ASTM, American Standard for Testing and Materials, E1052-96 Reapproved in 2002). The study was conducted at the University of Bosque where the virucidal efficacy of the test solution was tested against the three viruses: Herpes Simplex Virus type 2 (HSV-2, a DNA virus), Vesicular Stomatitis Virus (VSV, a RNA Virus), and Enterovirus-71 (EV-71, a RNA Virus). The study results are in Table 2 and it was concluded that the test solution eliminated each virus with high efficacy while demonstrating no adverse effects to the host cells.

TABLE 2

| | Efficacy at 30 seconds | | |
|---|---|---|---|
| Antiseptic Ability | Control of Innoculum | After treatment with 0.046% HOCl aqueous solution | |
| Microorganism | Population | Log Reduction | % Reduction |
| Herpes Simplex Virus (HSV type 2) | $3.4 \times 10^7$ | 7.53 | 99.9999% |
| Vesicular Stomatitis Virus (VSV) | $4.6 \times 10^7$ | 7.66 | 99.9999% |
| Enterovirus-71 (EV-71) | $6.91 \times 10^4$ | 4.83 | 99.998% |

Example 3. Biocompatibility and Safety Data

Oral, dermal, inhalation, eye, chronic, and teratogenicity toxicity studies were performed. Table 3. contains the results.

Acute and sub-chronic toxicity studies on Wister rats and New Zealand rabbits has established LD50>5000 mg/kg. The solution has been tested at 5000, 2500, and 1250 mg/kg. This research was performed according to the GLP and consistent with the evaluation of toxic substances established by the U.S. Environmental Protection Agency (EPA) and local regulators in Colombia.

TABLE 3

| Test | Animal Model | Exposure/Dose | Results |
|---|---|---|---|
| Acute Oral Toxicity | Wistar Rats | 5000 mg/Kg of HOCl Solution | The acute median lethal dose $LD_{50}$ of 0.05% concentration HOCl aqueous solutions was demonstrated to be greater than 5000 mg/kg of body weight of HOCl solution for both males and females. |
| Acute Dermal Toxicity | Albino New Zealand Rabbits | 5000 mg/Kg of HOCl Solution | The Acute Lethal Dose was demonstrated to be greater than 5000 mg/kg body weight for males and females. During postmortem macroscopic evaluations, no abnormalities were revealed in any test animal. |

TABLE 3-continued

| Test | Animal Model | Exposure/Dose | Results |
|---|---|---|---|
| Acute Inhalation Toxicity | Young Adult Wistar Rats | Gravimetric Chamber concentration 2.07 mg/L of HOCl | Animals All animals survived exposure to the test atmosphere. The Acute Inhalation $LC_{50}$ is greater than 2.07 mg/L of HOCl in male and female rats. |
| Acute Eye Irritation Study | Albino New Zealand Rabbits | 0.1 mL of a 5000 ppm solution of hypochlorous acid was used. The eyes of the animals were not washed after the administration of the test substance | Observations for ocular irritations were made at 1, 2, 3, 4, 7, 14, 21 days. Was determined not to be an irritant |
| Sub. Chronic Toxicity. 90 days. | Young adult Wistar Rats | 1000 mg/Kg Body weight | No mortalities, considered non-toxic |
| Teratogenicity | Females and Pregnant Wistar rats | Oral administration of 1000 mg/Kg/day | No mortalities, considered non-toxic |

Table 3 is showing the safety profile of 0.05% HOCl concentration aqueous solutions. These studies meets the requirements of 40 CRF part 160: U.S. EPA (FIFRA), 1989; OECD, Principles of GLP (as revised in 1997) published in ENV/MC/CHEM (98)17, OECD, Paris 1998 and all GLP requirements of the 40 CFR 792: U.S. EPA standards.

Table 3 is showing the safety profile of 0.05% HOCl concentration aqueous solutions. These studies meets the requirements of 40 CRF part 160: U.S. EPA (FIFRA), 1989; OECD, Principles of GLP (as revised in 1997) published in ENV/MC/CHEM (98)17, OECD, Paris 1998 and all GLP requirements of the 40 CFR 792: U.S. EPA standards.

Example 4. Intravenous Toxicity Study—Rat

This Study was conducted under the standards of Good Laboratory Practices related to experimental work in the evaluation of toxic substances, established by the EPA (Environmental Protection Agency, USA) communications 40 CRF parts 160 and 792 and the OECD (Organization for Economic Cooperation and Development UE) "Quality Assurance and GLP" guide.

A stabilized hypochlorous acid solution (300 ppm/0.03% HOCl) was tested intravenously in three different concentrations to Wister rats of both sexes that were grouped into 3 randomized groups in 3 different concentrations. Each group included 6 female and 6 male rats. The females were not pregnant. The objective of this study was to measure and determine the potential systemic toxicity in rats. The product was administered once a day for four days (0, 2, 4, 6).

Group 1: Each rat was inoculated intravenously with 1 dose on 4 different days, in the marginal tail vein, in volume per animal of 2.8 mL/kg of live weight, at a concentration of 10 mL of product in physiological saline solution total qs 100 mL.

Group 2: Each rat was inoculated intravenously with 1 dose on 4 different days in the marginal tail vein, in volume per animal 1.4 mL/kg live weight, at a concentration of 10 mL of the product in saline solution physiological total qs 100 mL.

Group 3: Each rat was inoculated intravenously with 1 dose on 4 different days in the marginal tail vein, in volume per animal 0.7 mL/kg live weight, at a concentration of 10 mL of the product in saline solution physiological total qs 100 mL.

At the end of the test all the surviving animals were sacrificed without suffering. During the time of the test there was no mortality in animals treated with the intravenous HOCl solution composition in any of the concentrations studied.

Observations: Animals were observed for mortality and signs of pharmacotoxicity frequently during the first 5 hours and then twice daily for 14 consecutive days. At the end of the period they were sacrificed for laboratory analysis and histopathology including blood chemistry, partial urine, complete blood count and histopathology of liver, kidney and bone marrow. The weight of the animals was taken on the day of dosing, at 7 days and before sacrifice.

Necropsy: At necropsy all the organs of the animals were examined macroscopically: Heart, lung, brain, cerebellum, spleen, liver, urinary bladder, kidneys, stomach, small intestine, large intestine, and reproductive organs.

Results Group 1: After the administration of the product the animals presented normal behavior and appearance. During the study there were no signs of systemic toxicity. Mortality for this dosage was 0% for both sexes. Kidney and Liver: Slight, small generalized congestive changes were observed.

Results Group 2: After the administration of the product the animals presented normal behavior and appearance. During the study there were no signs of systemic toxicity. Mortality for this dosage was 0% for both sexes.

Results Group number 3: After the administration of the product the animals presented normal behavior and appearance. During the study there were no signs of systemic toxicity. Mortality was 0% both for sexes. At necropsy all animal organs were examined macroscopically: heart, lung, brain, cerebellum, spleen, liver, bladder, urinary, kidneys, stomach, small intestine, large intestine, reproductive organs. They were all observed and determined normal. No macroscopic damage from the autopsy was observed. Complete blood count and biomarkers from blood (BUN, Creatinine, etc.) were all determined normal and within range.

Conclusions: During the study time the animals of the 3 test groups showed normal behavior, compared to the control animals, there was no characteristic symptomatology of organic damage or systemic toxicity. At necropsy the organs appear apparently normal. Weight gain was normal in all study groups. Group 1 experienced small-generalized congestive changes of the kidney and liver.

General Toxicology conclusions: The product performed well in toxicology studies and appears to be metabolized effectively by the animals. Based on current data and toxicology studies performed, toxicity was identified in some cases between dosing levels 2.4 ml/kg-2.8 ml/kg and above after repeated dosing. Recommended dosing is roughly 1 ml/kg (0.5 ml/kg-1.5 ml/kg) concluding that to reach toxicity, dosing will have to increase by an average multiple of at least 2.4, 2.8, or greater. Not wishing to be bound by theory, the cause of toxicity is believed to be high amounts of salt compounds from hypochlorous acid/hypochlorite. Therefore we identified that by diluting the compound in greater amounts of vehicle and use a slower infusion improved toxicity results and the ability of the host to effectively metabolize the compound solution.

Example 5

A discovery study was conducted analyzing the stabilized hypochlorous acid solution (300 ppm/0.03% HOCl) efficacy in several pathologies. Thirty-four (34) animals were selected that were diagnosed with hemoparasites, bacterial infections, viral infections, or immunocompromised conditions (Table 4). Animals underwent a standard dose regime for their condition.

TABLE 4

| Animal | Diagnosis | Number |
|---|---|---|
| Canines | Leishmaniasis | 16 |
| Canines | Parvovirosis | 2 |
| Canines | Bacterial Sepsis | 2 |
| Canines | Breast Carcinoma | 1 |
| Canines | Papillomatosis | 1 |
| Equidae (Horses) | Trypanosomiasis | 6 |
| Equidae (Horses) | Babesia, Borrelia Burgdorferi | 6 |

Results: The study concluded that the product under standard dosing regimes was effective in treating various types of pathogens. It was identified that the solution exerts a direct bactericidal effect, decreases the capacity for parasitic proliferation, and was an excellent adjuvant with the different conventional treatments improving the subject's condition and potentiating the microbicidal effect.

In animals with hemoparasites and bacterial infections (*trypanosoma* spp, *babesia* spp, bb and leishmaniosis) the solution improved the animals' conditions, lowered bacterial CPU and produced clinical cures. The treatment exerts a better immune response in canine subjects with visceral and cutaneous leishmaniosis than those treated with Miltefosine or Glucantime. The treatment eliminated the parasite and recovered the tissue at the site of the lesion.

The intravenous solution belongs to the "reactive oxygen species" ROS group, effective to combat trypanosomiasis in horses, shown with an increase in platelets, hematocrits and red blood cells.

Table 5 reports the results for the treatment of *Babesia* spp. in a horse subject.

TABLE 5

| Test | Result (before) | Result (after) | Reference Value |
|---|---|---|---|
| Red Blood Cells | 6.9 cell × 10e12/l | 8.3 cell × 10e 12/l | 6.4-10 cell × 10e12/l |
| Hematocrit | 28.2 L/L | 35.4 L/L | 32-47 L/L |
| Platelets | 86,000 | 141,000 | 100,000-270,000 |
| Hermoparasite | Positive for Babesia spp. | Negative for Babesia spp. | |

Table 6 reports the results for the treatment of a canine subject suffering from superficial bacterial infections secondary to carcinoma.

TABLE 6

| Test | Result (before) | Result (after) | Reference Value |
|---|---|---|---|
| Red Blood Cells | 3.5 cell × 10e12/l | 3.7 cell × 10e12/l | 4.5-10.3 cell × 10e12/l |
| Hematocrit | 24% | 24% | 38-53% |
| White Blood Cells | 19.8 × 10 3 Cell | 37.5 × 10 3 Cell | 7.3-13 × 10 3 Cell |
| Neutrophils | 110088 cell/µl | 18750 cell/µl | 4599-9490 cell/µl |
| ALT[1] | 113.3 | 32.4 | 1-37 |
| AST[2] | 76.3 | 75.2 | 3-41 |
| Ctreatinine | 0.9 | 1.2 | 0.2-2.1 |
| BUN[3] | 9.3 | 6.7 | 1-28 |

[1] Alanine aminotransferase.

[2] Aspartate aminotransferase.

[3] Blood urine nitrogen.

Out of 34 animals, 92% made full recovery as biomarkers from blood returned to normal ranges. In animals with viral infections or carcinoma, the state of each animal improved greatly and showed decreased physical signs of symptoms. Biomarkers from blood improved and returned to normal ranges. In all cases it was determined that the treatment improved the subject's condition, increased energy capacity, decreased immunosuppression, and acted as an immunogenic and/or immunomodulatory solution.

Conclusions: The study demonstrated initial efficacy in canines and horses with hemoparasites, bacterial infections, and viral infections. It improves and can regulate the immune system. Treatment improves visual and physical condition of the patient. There were no reported side effects in the 34 animals studied.

The compositions and methods disclosed herein include(s) at least the following aspects:

Aspect 1: An intravenous solution composition, comprising, consisting essentially of, or consisting of, about 0.010% to about 0.040% hypochlorous acid (HOCl); about 0.05 to about 0.35% in NaCl; about 0.005% to about 0.020% in OCl; and water, wherein all the % are by percentage over the total volume of the intravenous solution, and wherein the composition has a pH of about 5.2 to about 6.2.

Aspect 2: The intravenous solution composition of Aspect 1, comprising about 0.020% to about 0.030% hypochlorous acid (HOCl); about 0.15 to about 0.25% in NaCl; about 0.010% to about 0.020% in OCl; and water, and wherein the composition has a pH of about 5.2 to about 6.2.

Aspect 3: The intravenous solution composition of Aspect 1 or 2, comprising about 0.022% to about 0.028% hypochlorous acid (HOCl); about 0.18 to about 0.22% in NaCl; about 0.012% to about 0.018% in OCl; and water, wherein the composition has a pH of about 5.5 to about 6.0.

Aspect 4: The intravenous solution composition of any one of Aspects 1-3 having a shelf life of up to 3, 4, 5, 6, 7, 8, 9, 10, 11, 12, or more months when packaged in a sterile glass vial and stored under conditions of 20° C., specifically up to 3 months.

Aspect 5: The intravenous solution composition of any one of Aspects 1-4, further combined with a pharmaceutically acceptable intravenous vehicle, wherein the pharmaceutically acceptable intravenous vehicle is water for injection, specifically nonpyrogenic sterile water for injection.

Aspect 6: The intravenous solution composition of any one of Aspects 1-5, wherein the intravenous composition is free of or substantially free of one or more of sodium hypochlorite (NaHClO$_3$), ozone (O$_3$), hydrogen peroxide (H$_2$O$_2$), sodium hydroxide (NaOH), or a combination thereof.

Aspect 7: A kit comprising, the intravenous solution composition of any one of Aspects 1-6 packaged in a container and optionally further comprising information for providing the intravenous solution composition to a subject in need thereof.

Aspect 8: A method of treating an infection, comprising providing an effective amount of the intravenous solution composition of any one of Aspects 1-6 to a subject in need thereof.

Aspect 9: The method of Aspect 8, wherein the infection to be treated is a bacterial infection, a fungal infection, a viral infection, a bacterial spore infection, a parasitic infection, or a combination thereof.

Aspect 10: The method of Aspect 8 or 9, wherein the hypochlorous acid intravenous solution is effective against antibiotic-resistant, antifungal-resistant, and antiviral-resistant species.

Aspect 11: The method of Aspect 8 or 9, wherein the infection is caused by gram negative bacteria, gram positive bacteria, *Escherichia coli, Campylobacter rectus, Enterobacter cloacae, Enterococcus faecalis, Enterococcus faecium, Klebsiella oxytoca, Klebsiella pneumoniae, Staphylococcus aureus*, methicillin-resistant *Staphylococcus aureus, Pseudomonas aeruginosa, Salmonella enteritidis, Staphylococcus epidermidis, Streptococcus pyogenes, Treponema pallidum* (syphilis), vancomycin-resistant enterococci, or a combination thereof; Herpes simplex virus type-2 and type-1, human immunodeficiency virus (HIV), human papilloma virus (HPV), Hepatitis B and C virus, Bovine Diarrhea virus, molluscum contagiosum, respiratory viruses such as influenza viruses (e.g. H1N1), coronavirus, Zika virus, Ebola virus, or a combination thereof; *Aspergillus niger, Candida albicans, Trichophyton mentagrophytes*, or a combination thereof; or Trichomoniasis, leishmaniasis, or a combination thereof; or a combination thereof.

Aspect 12: A method of augmenting the immune system of a subject, comprising providing an effective amount of the intravenous solution of any one of Aspects 1-6 to a subject in need thereof.

Aspect 13: The method of Aspect 12, wherein the subject has an infectious disease, is at risk of contracting an infectious disease, is receiving cancer treatment, chemotherapy, radiation therapy, will undergo surgery, or a combination thereof.

Aspect 14: A method of preventing bacterial or fungal contamination, bacterial or fungal infection, or sepsis in a subject, comprising providing an effective amount of the intravenous solution composition of any one of Aspects 1-6 to a subject in need thereof.

Aspect 15: A method for treating cancer in a subject, comprising providing an effective amount of the intravenous solution composition of any one of Aspects 1-6 to a subject in need thereof.

Aspect 16: The method of any one of Aspects 8-15, wherein the intravenous solution composition is further combined with a pharmaceutically acceptable intravenous vehicle, wherein the pharmaceutically acceptable intravenous vehicle is water for injection, specifically nonpyrogenic sterile water for injection prior to use.

Aspect 17: The method of any one of Aspects 8-15, wherein the intravenous solution composition of any one of Aspects 1-4 is provided to the subject in an amount of about 1 to about 20 ml of the intravenous solution composition once per day for a total of about 4 to about 6 doses; or once every 48 hours for a total of about 4 to about 6 doses.

Aspect 18: The method of Aspect 16, wherein the intravenous solution composition is provided to the subject in an amount of about 1 to about 20 ml of the intravenous solution composition once per day for a total of about 4 to about 6 doses; or once every 48 hours for a total of about 4 to about 6 doses; and wherein the intravenous solution composition is diluted in up to 100 ml of a pharmaceutically acceptable intravenous vehicle, specifically about 20 to about 85 ml of a pharmaceutically acceptable intravenous vehicle.

Aspect 19: The method of any one of Aspects 8-15, wherein the intravenous solution composition of any one of Aspects 1-4, is provided to the subject in an amount of about 1 to about 20 ml, specifically about 10 ml of the intravenous solution composition in 1 dose every 24 to 48 hours for a total of about 4 to about 6 doses, e.g., as a general dose, for combination therapy, to treat a bacterial infection, or for one time use; and wherein the intravenous solution composition is diluted with a pharmaceutically acceptable intravenous vehicle up to about 100 ml total volume.

Aspect 20: The method of any one of Aspects 8-15, wherein the intravenous solution composition of any one of Aspects 1-4, is provided to the subject in an amount of about 1 to about 20 ml, specifically about 10 ml of the intravenous solution composition in 2 doses weekly for 2, 4, 6, 8, 10, or 12 weeks, or until conditions improve, e.g., for a chronic condition, a viral infection, a combination therapy, or cancer; optionally the subject may receive a loading dose during week 1, specifically a loading dose that is 1 dose for 4 days during week 1; and wherein the intravenous solution composition is diluted with a pharmaceutically acceptable intravenous vehicle up to about 100 ml total volume.

Aspect 21: The method of any one of Aspects 8-15, wherein the intravenous solution composition of any one of Aspects 1-4, is provided to the subject in an amount of about 1 to about 20 ml, specifically about 10 ml of the intravenous solution composition in 1 dose daily for 8 consecutive days, e.g., for an urgent condition for example bacterial sepsis or fungal sepsis; and wherein the intravenous solution composition is diluted with a pharmaceutically acceptable intravenous vehicle up to about 100 ml total volume. In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of treating an infection, comprising providing an effective amount of an intravenous solution composition to a subject in need thereof, the intravenous solution composition comprises
    about 0.010% to about 0.040% hypochlorous acid (HOCl);
    about 0.05 to about 0.35% in NaCl;
    about 0.005% to about 0.020% in OCl; and
    water,
    wherein all the % are by percentage over the total volume of the intravenous solution, and
    wherein the composition has a pH of about 5.2 to about 6.2; and
    wherein the intravenous solution composition is provided to the subject in an amount of about 1 to about 20 ml of the intravenous solution composition once per day for a total of about 4 to about 6 doses; or once every 48 hours for a total of about 4 to about 6 doses.

2. The method of claim 1, wherein the infection to be treated is a bacterial infection, a fungal infection, a viral infection, a bacterial spore infection, a parasitic infection, or a combination thereof.

3. The method of claim 1, wherein the hypochlorous acid intravenous solution is effective against antibiotic-resistant, antifungal-resistant, and antiviral-resistant species.

4. The method of claim 1, wherein the infection is caused by gram negative bacteria, gram positive bacteria, *Escherichia coli, Campylobacter rectus, Enterobacter cloacae, Enterococcus faecalis, Enterococcus faecium, Klebsiella oxytoca, Klebsiella pneumoniae, Staphylococcus aureus*, methicillin-resistant *Staphylococcus aureus, Pseudomonas aeruginosa, Salmonella enteritidis, Staphylococcus epidermidis, Streptococcus pyogenes, Treponema pallidum* (syphilis), vancomycin-resistant enterococci, or a combination thereof;
    Herpes simplex virus type-2 and type-1, human immunodeficiency virus (HIV), human papilloma virus (HPV), Hepatitis B and C virus, Bovine Diarrhea virus, molluscum contagiosum, respiratory viruses such as influenza viruses (e.g. H1N1), coronavirus, Zika virus, Ebola virus, or a combination thereof;
    *Aspergillus niger, Candida albicans, Trichophyton mentagrophytes*, or a combination thereof; or
    Trichomoniasis, leishmaniasis, or a combination thereof; or a combination thereof.

5. The method of claim 1, wherein the intravenous solution composition is further combined with a pharmaceutically acceptable intravenous vehicle, wherein the pharmaceutically acceptable intravenous vehicle is water for injection.

6. The method of claim 5, wherein the intravenous solution composition is provided to the subject in an amount of about 1 to about 20 ml of the intravenous solution composition once per day for a total of about 4 to about 6 doses; or once every 48 hours for a total of about 4 to about 6 doses; and wherein the intravenous solution composition is diluted in up to 100 ml of a pharmaceutically acceptable intravenous vehicle.

7. A method of augmenting the immune system of a subject, comprising providing an effective amount of the intravenous solution to a subject in need thereof, the intravenous solution composition comprises about 0.010% to about 0.040% hypochlorous acid (HOCl);
about 0.05 to about 0.35% in NaCl;
about 0.005% to about 0.020% in OCl; and
water,
wherein all the % are by percentage over the total volume of the intravenous solution, and
wherein the composition has a pH of about 5.2 to about 6.2; and
wherein the intravenous solution composition is provided to the subject in an amount of about 1 to about 20 ml of the intravenous solution composition once per day for a total of about 4 to about 6 doses; or once every 48 hours for a total of about 4 to about 6 doses.

8. The method of claim 7, wherein the subject has an infectious disease, is at risk of contracting an infectious disease, is receiving cancer treatment, chemotherapy, radiation therapy, will undergo surgery, or a combination thereof.

9. A method of treating bacterial or fungal contamination, bacterial or fungal infection, or sepsis in a subject, comprising providing an effective amount of the intravenous solution composition to a subject in need thereof, the intravenous solution composition comprises about 0.010% to about 0.040% hypochlorous acid (HOCl);
about 0.05 to about 0.35% in NaCl;
about 0.005% to about 0.020% in OCl; and
water,
wherein all the % are by percentage over the total volume of the intravenous solution, and
wherein the composition has a pH of about 5.2 to about 6.2; and
wherein the intravenous solution composition is provided to the subject in an amount of about 1 to about 20 ml of the intravenous solution composition once per day for a total of about 4 to about 6 doses; or once every 48 hours for a total of about 4 to about 6 doses.

10. A method for treating cancer in a subject, comprising providing an effective amount of the intravenous solution composition to a subject in need thereof, the intravenous solution composition comprises about 0.010% to about 0.040% hypochlorous acid (HOCl);
about 0.05 to about 0.35% in NaCl;
about 0.005% to about 0.020% in OCl; and
water,
wherein all the % are by percentage over the total volume of the intravenous solution, and
wherein the composition has a pH of about 5.2 to about 6.2; and
wherein the intravenous solution composition is provided to the subject in an amount of about 1 to about 20 ml of the intravenous solution composition once per day for a total of about 4 to about 6 doses; or once every 48 hours for a total of about 4 to about 6 doses.

* * * * *